United States Patent [19]

Tani et al.

[11] Patent Number: 5,095,149
[45] Date of Patent: Mar. 10, 1992

[54] PROCESS FOR PRODUCING 4-HALOGENO-2-ALKOXYIMINO-3-OXO FATTY ACID

[75] Inventors: Tsutomu Tani; Kazuo Maruhashi; Tsutomu Miyagawa, all of Kawagoe, Japan

[73] Assignee: Wako Pure Chemical Industries, Ltd., Osaka, Japan

[21] Appl. No.: 575,710

[22] Filed: Aug. 31, 1990

[30] Foreign Application Priority Data

Sep. 4, 1989 [JP] Japan .................................. 1-229013

[51] Int. Cl.$^5$ .......................................... C07C 241/00
[52] U.S. Cl. ................................................... 562/560
[58] Field of Search .......................... 560/312; 562/560

[56] References Cited

FOREIGN PATENT DOCUMENTS

| | | | |
|---|---|---|---|
| 0184257 | 11/1986 | European Pat. Off. | 560/312 |
| 0235878 | 9/1987 | European Pat. Off. | 560/312 |
| 0255297 | 3/1988 | European Pat. Off. | 560/312 |
| 53-103493 | 9/1978 | Japan . | |
| 54-98795 | 8/1979 | Japan . | |
| 56-145290 | 11/1981 | Japan . | |
| 61-143389 | 7/1986 | Japan . | |
| 61-55905 | 11/1986 | Japan . | |
| 62-273945 | 11/1987 | Japan . | |

OTHER PUBLICATIONS

Dahlbom et al., Acta Pharm. Succica 4, pp. 211–216, (1967).
Nilsson et al., Acta Pharm. Succica 7, pp. 239–246, (1970).
Kornet, Jour. of Pham. Sci., vol. 69, No. 6, pp. 729–731, Jun. 1980.
Nilsson et al., Acta Pharm. Succica 5, pp. 71–76, (1968).
Gauthier et al., Ann. Pharm. Francaises, 38, pp. 359–366, (1980).
Yoneda et al., Chem. Pham. Bull., 20(3), pp. 476–486, (1972).

*Primary Examiner*—Mary C. Lee
*Assistant Examiner*—Robert C. Whittenbaugh
*Attorney, Agent, or Firm*—Armstrong, Nikaido, Marmelstein, Kubovcik & Murray

[57] ABSTRACT

4-Halogeno-2-alkoxyimino-3-oxo fatty acid can be produced by one-pot and one-step by reacting a halogenating agent with a 2-alkoxyimino-3-oxo fatty acid ester in an ether solvent or a mixed solvent of an ether solvent and an inert organic solvent such as carbon tetrachloride, benzene, toluene, etc.

9 Claims, No Drawings

PROCESS FOR PRODUCING 4-HALOGENO-2-ALKOXYIMINO-3-OXO FATTY ACID

BACKGROUND OF THE INVENTION

The present invention relates to a novel process for producing a 4-halogeno-2-alkoxyimino-3-oxo fatty acid which is useful as an intermediate for synthesizing a cephalosporin antibiotic.

4-Halogeno-2-alkoxyimino-3-oxo fatty acids are important intermediates used for introducing an acyl group into the amino group at the 7-position of a cephalosporin antibiotic.

For example, 2-(2-amino-1,3-thiazol-4-yl)-2-methoxyiminoacetyl group now used as main modifying group is introduced mainly by the two methods described below, in both of which 4-halogeno-2-methoxyimino-3-oxobutyric acid is used as an intermediate. A first method comprises synthesizing 2-(2-amino-1,3-thiazol-4-yl)-2-methoxyiminoacetic acid by ring closure reaction of 4-halogeno-2-methoxyimino-3-oxobutyric acid with thiourea, protecting its amino group, converting the thus obtained compound into a reactive derivative such as acid chloride, and forming an amide linkage between the derivative and the amino group at the 7-position of a cephalosporin nucleus (Japanese Patent Appln. Kokai (Laid-Open) No. 53-103493). In a second method, the order of ring closure reaction and conversion to amide is reversed. That is, the second method comprises converting the amino group at the 7-position of a cephalosporin nucleus into an amide previously by use of a reactive derivative of 4-halogeno-2-methoxyimino-3-oxobutyric acid, and acting thiourea on the thus obtained compound to carry out ring closure reaction (Japanese Patent Appln. Kokai (Laid-Open) Nos. 54-98795 and 61-143389).

In addition, 2-(2-hydroxy-1,3-thiazol-4-yl)-2-methoxyiminoacetyl group obtained by converting the amino group of the above 2-(2-amino-1,3-thiazol-4-yl)-2-methoxyiminoacetyl group is also used as a group for modifying cephalosporin antibiotics. Also in this case, 4-halogeno-2-methoxyimino-3-oxobutyric acid is used as an intermediate in the same manner as described above, except for acting a thiocarbamic acid ester in place of thiourea.

The 4-halogeno-2-alkoxyimino-3-oxo fatty acids are thus very important intermediates for producing cephalosporin antibiotics, but their production processes should be improved in many respects.

For example, Japanese Patent Appln. Kokai (Laid-Open) No. 54-98795 has disclosed a process for synthesizing 4-bromo-2-methoxyimino-3-oxobutyric acid which comprises direct bromination of 2-methoxyimino-3-oxobutyric acid. Since the starting material i.e., 2-methoxyimino-3-oxobutyric acid is obtained usually in the form of methyl ester or ethyl ester, the methyl or ethyl ester should be hydrolyzed by use of an alkali hydroxide before the bromination reaction, and therefore troublesome operations are required. Moreover, unlike the desired compound 4-bromo-2-methoxyimino-3-oxobutyric acid, 2-methoxyimino-3-oxobutyric acid is not stable in the form of a free acid and hence is susceptible to various decompositions during the ester decomposition reaction or a subsequent isolation procedure. Therefore, it is difficult to obtain 4-bromo-2-methoxyimino-3-oxobutyric acid of high purity in high yield.

On the other hand, as to the latter problem between the above problems, Japanese Patent Appln. Kokai (Laid-Open) No. 56-145290 has disclosed, as a process in which the decompositions of 2-methoxyimino-3-oxobutyric acid are prevented, a process which comprises subjecting tert-butyl ester of 2-methoxyimino-3-oxobutyric acid to ester decomposition in trifluoroacetic acid to obtain free acid, distilling off the trifluoroacetic acid, thereafter reacting bromine with the free acid in acetic acid and hydrobromic acid, and thereby producing 4-bromo-2-methoxyimino-3-oxobutyric acid. In this process, excessive decomposition of 2-methoxyimino-3-oxobutyric acid by water is prevented by obtaining the free acid without hydrolysis by taking advantage of the fact that under acidic conditions, the tert-butyl group of the tert-butyl ester is liberated as isobutylene. This process, however, is disadvantageous, for example, in that it uses trifluoroacetic acid which is highly toxic and corrosive, and that unstable 2-methoxyimino-3-oxobutyric acid should be heat-treated for distilling off the trifluoroacetic acid. Furthermore, this process is not yet free from troublesome operations.

SUMMARY OF THE INVENTION

The present invention is intended to solve such problems of conventional processes and provide a process for producing a 4-halogeno-2-alkoxyimino-3-oxo fatty acid easily in high yield.

The present invention provides a one-pot one-step process for producing a 4-halogeno-2-alkoxyimino-3-oxo fatty acid of the general formula:

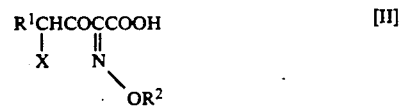

wherein X is a halogen atom; $R^1$ is a hydrogen atom, a linear or branched alkyl group, a cyclic alkyl group, an aryl group or an aralkyl group; and $R^2$ is a substituted or unsubstituted, linear or branched alkyl group, a substituted or unsubstituted cyclic alkyl group, a substituted or unsubstituted aryl group, or a substituted or unsubstituted aralkyl group, which comprises reacting a halogenating agent with a 2-alkoxyimino-3-oxo fatty acid ester of the formula:

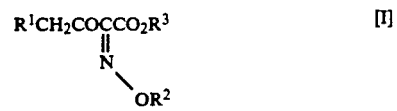

wherein $R^1$ and $R^2$ are as defined above; and $R^3$ is a tertiary alkyl group, in an ether solvent or a mixed solvent of an ether solvent and an inert organic solvent, and thereby carrying out cleavage of the ester linkage and halogenation of the carbon at the 4-position simultaneously.

DESCRIPTION OF THE PREFERRED EMBODIMENTS

According to the present invention, there are utilized the fact that when a tertiary alkyl ester of a fatty acid is decomposed by an acid, the tertiary alkyl group is liberated not as alcohol but as alkene, and the fact that the alkene becomes an alkylene dihalide immediately through its addition reaction with a halogen. In detail, a halogenating agent is reacted directly with a tertiary alkyl ester of a fatty acid to convert a partly liberated alkene into an alkylene dihalide successively, whereby alkene is produced. Therefore, liberation of the alkyl group is accelerated and halogenation reaction and ester decomposition reaction proceed at the same time. When a halogenating agent is reacted directly with a tertiary alkyl ester of 2-alkoxyimino-3-oxo fatty acid in an ether solvent or a mixed solvent of an ether solvent and an inert organic solvent, a 4-halogeno-2-alkoxyimino-3-oxo fatty acid can be obtained by one pot one-step without isolating free fatty acid.

The constitution of the present invention is explained below in detail.

As $R^1$ in the general formula:

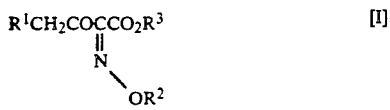

[I]

used in the present invention includes, there can be exemplified hydrogen atom; alkyl groups such as methyl, ethyl, propyl, isopropyl, tert-butyl, octyl, dodecyl, etc.; cyclic alkyl groups such as cyclopropyl, cyclopentyl, cyclohexyl, etc.; aryl groups such as phenyl, tolyl, xylyl, naphthyl, etc.; and aralkyl groups such as benzyl, phenetyl, etc. As $R^2$, there can be exemplified substituted or unsubstituted alkyl groups such as methyl, methoxymethyl, methylthiomethyl, ethyl, isopropyl, tert-butyl, octyl, dodecyl, etc.; substituted or unsubstituted cyclic alkyl groups such as cyclopropyl, cyclopentyl, cyclohexyl, 4-methylcyclohexyl, etc.; substituted or unsubstituted aryl groups such as phenyl, 4-chlorophenyl, 2-methoxyphenyl, tolyl, xylyl, naphthyl, etc.; and substituted or unsubstituted aralkyl groups such as benzyl, 4-chlorobenzyl, 2-methoxybenzyl, phenethyl, etc. As $R^3$, there can be exemplified tertiary alkyl groups such as tert-butyl, tert-amyl, 1,1-dimethylbutyl, etc.

The ether solvent used in the present invention includes, for example, dimethyl ether, diethyl ether, diisopropyl ether, dibutyl ether, tetrahydrofuran, dioxane, and diethylene glycol dimethyl ether. Of these, diisopropyl ether is particularly preferable.

As the inert organic solvent usable as a mixed solvent with the ether solvent, any solvent may be used so long as it can dissolve the 2-alkoxyimino-3-oxo fatty acid ester and does not inhibit the ester decomposition reaction and the halogenation reaction, and there can be exemplified halogenated hydrocarbons such as carbon tetrachloride, chloroform, dichloromethane, 1,2-dichloroethane, etc.; aromatic hydrocarbons such as benzene, toluene, xylene, etc.; and linear of cyclic saturated hydrocarbons such as n-pentane, n-hexane, cyclopentane, cyclohexane, etc. Of these, the halogenated hydrocarbons are particularly preferable. As to the mixing ratio between the ether solvent and the inert organic solvent, it is sufficient that the ether solvent is present in such an amount as does not hinder the reaction. Preferable mixing ratio is 9 parts by volume or less, more preferably 5 parts by volume or less, of the inert organic solvent per part by volume of the ether solvent.

The halogenating agent used in this invention includes, for example, halogen molecules such as chlorine, bromine, iodine, etc.; and sulfuryl halides such as sulfuryl chloride, sulfuryl bromide, etc. Of these, chlorine or bromine is particularly preferable.

The 2-alkoxyimino-3-oxo fatty acid ester of the general formula [I] used as starting material in this invention can easily be synthesized, for example, by reacting a corresponding 3-oxo fatty acid ester with sodium nitrite in glacial acetic acid to convert the same into 2-hydroxyimino-3-oxo fatty acid ester, and then reacting therewith an alkylating agent such as dialkyl sulfate or alkyl halide in the presence of a basic substance. It is sufficient that the product thus synthesized is used.

The production process of the present invention can easily be practiced, for example, in the following manner.

First, the 2-alkoxyimino-3-oxo fatty acid ester of the general formula [I] is dissolved in an ether solvent or mixed solvent containing an ether solvent 2 to 5 times, preferably 2 to 3 times, as much as the ester, and the halogenating agent is added dropwise with stirring in an amount of 1.5 to 3 moles per mole of the starting 1 20 ester at $-30°$ C. to $80°$ C., preferably $-10°$ C. to $40°$ C., over a period of approximately 1-4 hours. Then, the resulting mixture was stirred at the same temperature or room temperature for 2 to 25 hours and thereafter washed with water to be separated, whereby the water-soluble by-products are removed. In this case, for example, a water-insoluble solvent which permits extraction of a desired compound may also be added for preventing the desired compound from dissolving in the aqueous layer. The organic layer thus obtained is treated with a suitable drying agent, and the solvent is optionally distilled off under reduced pressure, whereby a residue composed mainly of the desired compound 4-halogeno-2-alkoxyimino-3-oxo fatty acid of the formula:

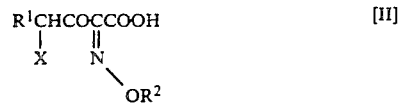

[II]

wherein X is a halogen atom; $R^1$ is a hydrogen atom, a linear or branched alkyl group, a cyclic alkyl group, an aryl group or an aralkyl group; and $R^2$ is a substituted or unsubstituted, linear or branched alkyl group, a substituted or unsubstituted cyclic alkyl group, a substituted or unsubstituted aryl group, or a substituted or unsubstituted aralkyl group, is obtained in the form of paste or an oily substance.

The desired compound is isolated from the residue by a conventional method. When solid, the desired compound is isolated by recrystallization from xylene or the like. When liquid, the desired compound is isolated by decantation by use of a solvent capable of dissolving the starting material and impurities selectively, for example, n-hexane.

Examples are described below but they are not intended in any way to limit the scope of the present invention.

EXAMPLE 1

(1) Synthesis of tert-butyl 2-methoxyimino-3-oxobutyrate

In 31.6 g of glacial acetic acid was dissolved 31.6 g (0.2 mole) of tert-butyl acetoacetate, and a solution of 15.2 g (0.22 mole) of sodium nitrite in 30 ml of water was added dropwise at $0°$ to $5°$ C. over a period of 2 hours and stirred at room temperature for 1 hour. After completion of the reaction, 100 ml of water and 100 ml of dichloromethane were added and then stirred, and the resulting mixture was allowed to stand to be separated and the aqueous layer was removed. To the thus obtained solution of tert-butyl 2-hydroxyimino-3-oxobutyrate in dichloromethane was added 41.5 g (0.3 mole) of potassium carbonate with cooling, after which 27.8 g (0.22 mole) of dimethyl sulfate was added dropwise at 20° C. over a period of 2 hours and stirred at 20° C. for another 1 hour. After completion of the reaction, the reaction solution was washed with 150 ml of water and dried over anhydrous magnesium sulfate, and then the solvent was distilled off under reduced pressure to obtain 38.0 g (yield 95%) of tert-butyl 2-methoxyimino-3-oxobutyrate as a light-yellow, oily substance.

(2) Synthesis of 4-bromo-2-methoxyimino-3-oxobutyric acid

In 50 ml of diisopropyl ether was dissolved 20.1 g (0.1 mole) of tert-butyl 2-methoxyimino-3-oxobutyrate, and 32.0 g (0.2 mole) of bromine was added dropwise at 0° to 5° C. over a period of 1 hour and 30 minutes and stirred at 0° to 5° C. for 2 hours. After completion of the reaction, 25 ml of water was added and then stirred to conduct washing, whereby water-soluble by-products were removed.

The organic layer was dried over anhydrous magnesium sulfate, after which the solvent was distilled off under reduced pressure and the residue was crystallized from 50 ml of xylene to obtain 9.5 g (yield 42.4%) of 4-bromo-2-methoxyimino-3-oxobutyric acid as white crystals.

Melting point 76° -78° C.

NMR (CDCl$_3$): δ ppm 4.21 (3H, s, —OCH$_{-3}$), 4.38 (2H, s, BrCH$_{-2}$CO—), 10.59 (1H s, —COO$\underline{H}$).

IR (KBr): 2930, 1735, 1710, 1595, 1045 cm$^{-1}$.

EXAMPLE 2

(1) Synthesis of tert-butyl 2-methoxyimino-3-oxo-4-phenylbutyrate 50 9 Grams (yield 92%) of tert-butyl 2-methoxyimino-3-oxo-4-phenylbutyrate was obtained as a light-yellow oily substance by carrying out reaction and after-treatment in exactly the same manner as in Example 1 (1), except for using 46.8 g (0.2 mole) of tert-butyl 3-oxo-4-phenylbutyrate in place of 1.6 g (0.2 mole) of tert-butyl acetoacetate.

(2) Synthesis of 4-bromo-2-methoxyimino-3-oxo-4-phenylbutyric acid

In 50 ml of diisopropyl ether was dissolved 27.7 g (0.1 mole) of tert-butyl 2-methoxyimino-3-oxo-4-phenylbutyrate, and 32.0 g (0.2 mole) of bromine was added dropwise at 0° to 5° C. over a period of 1 hour and 50 minutes and then stirred at 0° to 5° C. for 2 hours. After completion of the reaction, 25 ml of water was added and then stirred to conduct washing, whereby water-soluble by-products were removed.

Thereafter, the organic layer was treated in the same manner as in Example 1, (2) to obtain 15.7 g (yield 44.1%) of 4-bromo-2-methoxyimino-3-oxo-4-phenylbutyric acid as white crystals.

EXAMPLE 3

(1) Synthesis of tert-butyl 2-benzyloxyimino-3-oxobutyrate

A solution of tert-butyl 2-hydroxyimino-3-oxobutyrate in dichloromethane was obtained in the same manner as in Example 1, (1) by using 31.6 g (0.2 mole) of tert-butyl acetoacetate. To said solution was added 41.5 g (0.3 mole) of potassium carbonate with cooling, after which 34.2 g (0.2 mole) of benzyl bromide was added dropwise at 15° to 20° C. over a period of 2 hours and stirred at 30° to 35° C. for another 10 hours. After completion of the reaction, 150 ml of water was added to conduct washing and separation and the solution in dichloromethane thus obtained was dried over anhydrous magnesium sulfate. Then, the solvent was distilled off under reduced pressure to obtain 41.5 g (yield 93%) of tert-butyl 2-benzyloxyimino-3-oxobutyrate as a light-yellow, oily substance.

(2) Synthesis of 2-benzyloxyimino-4-bromo-3-oxobutyric acid

In 50 ml of diisopropyl ether was dissolved 27.7 g (0.1 mole) of tert-butyl 2-benzyloxyimino-3-oxobutyrate, and 32.0 g (0.2 mole) of bromine was added dropwise at 0° to 5° C. over a period of 1 hour and 30 minutes and stirred at 0° to 5° C. for 2 hours. After completion of the reaction, 25 ml of water was added and then stirred to conduct washing, whereby water-soluble by-products were removed.

Thereafter, the organic layer was treated in the same manner as in Example 1, (2) to obtain 15.4 g of 2-benzyloxyimino-4-bromo-3-oxobutyric acid as a light-yellow, syrup-like substance (yield: 43.1%). On analysis, the purity of the desired compound was found to be 96.3%.

NMR (CDCl$_3$)δ ppm 4.30 (2H, s, BrCH$_{-2}$—), 5.36. (2H, s, —OCH$_{-2}$C$_6$H$_5$), 7.33 (5H, s, —C$_6$H$_{-5}$), 9.18 (1H, s, —COOH).

IR (neat): 3020, 1740, 1720, 1600, 1020 cm$^{-1}$.

EXAMPLE 4

In 50 ml of diisopropyl ether was dissolved 22.9 g (0.1 mole) of 1,1-dimethylbutyl 2-methoxyimino-3-oxobutyrate, and 32.0 g (0.2 mole) of bromine was added dropwise at 0° to 5° C. over a period of 1 hour and 30 minutes and stirred at 0° to 5° C. for 2 hours. After completion of the reaction, 25 ml of water was added and then stirred to conduct washing, whereby water-soluble by-products were removed.

Thereafter, the organic layer was treated in the same manner as in Example 1, (2) to obtain 9.7 g (yield 43.3%) of 4-bromo-2-methoxyimino-3-oxobutyric acid as white crystals.

EXAMPLE 5

In 50 ml of 1,4-dioxane was dissolved 20.1 g (0.1 mole) of tert-butyl 2-methoxyimino-3-oxobutyrate, and 32.0 g (0.2 mole) of bromine was added dropwise at 0° to 5° C. over a period of 1 hour and 30 minutes and stirred at 20° C. for 20 hours. After completion of the reaction, 25 ml of a saturated aqueous sodium chloride solution and 50 ml of 1,2-dichloroethane were added and then stirred, and the resulting mixture was allowed to stand and then separated and the aqueous layer was removed. The organic layer was further washed with 25 ml of water and dried over anhydrous magnesium sulfate, after which the 1,2-dichloroethane was distilled off under reduced pressure, and the residue was crystallized from 50 ml of xylene to obtain 9.2 g (yield 41.1%) of 4-bromo-2-methoxyimino-3-oxobutyric acid as white crystals.

EXAMPLE 6

In a mixture of 25 ml of diisopropyl ether and 25 ml of 1,2-dichloroethane was dissolved 20.1 g (0.1 mole) of tert-butyl 2-methoxyimino-3-oxobutyrate, and 32.0 g (0.2 mole) of bromine was added dropwise at 0° to 5° C. over a period of 1 hour and 30 minutes and stirred at 0° to 5° C. for 2 hours. After completion of the reaction, 25 ml of water was added and then stirred to conduct washing, whereby water-soluble by-products were removed.

Thereafter, the organic layer was treated in the same manner as in Example 1, (2) to obtain 10.4 g (yield 46.4%) of 4-bromo-2-methoxyimino-3-oxobutyric acid as white crystals.

EXAMPLE 7

In a mixture of 10 ml of diisopropyl ether and 40 ml of chloroform was dissolved 20.1 g (0.1 mole) of tert-butyl 2-methoxyimino-3-oxobutyrate, and 32.0 g (0.2 mole) of bromine was added dropwise at 0° to 5° C. over a period of 1 hour and 30 minutes and stirred at 0° to 5° C. for 2 hours. After completion of the reaction, 25 ml of water was added and then stirred to conduct washing, whereby water-soluble by-products were removed.

Thereafter, the organic layer was treated in the same manner as in Example 1, (2) to obtain 10.2 g (yield 45.5%) of 4-bromo-2-methoxyimino-3-oxobutyric acid as white crystals.

EXAMPLE 8

In 50 ml of diisopropyl ether was dissolved 20.1 g (0.1 mole) of tert-butyl 2-methoxyimino-3-oxobutyrate, and 32.0 g (0.45 mole) of chlorine gas was introduced to the solution at 0° to 5° C. over a period of 4 hours. After completion of the introduction, 30 ml of water was added and then stirred to conduct washing, whereby water-soluble by-products were removed.

Subsequently, the organic layer was dried over anhydrous magnesium sulfate, after which the solvent was distilled off under reduced pressure and 60 ml of n-hexane was added to the residue to extract and remove impurities. The residual n-hexane was distilled off under reduced pressure to obtain 12.8 g of 4-chloro-2-methoxyimino-3-oxobutyric acid as a yellow, oily substance (yield: 71.3%). On analysis, the purity of the desired compound was found to be 95.2%.

NMR (CDCl$_3$)δ ppm 4.17 (3H, s, —OCH$_3$), 4.61 (2H, s, ClCH$_2$CO—), 8.53 (1H, bs, —COO$\underline{H}$).

IR (neat): 3000, 1730, 1705, 1600, 1040 cm$^{-1}$.

EXAMPLE 9

In 50 ml of diisopropyl ether was dissolved 20.1 g (0.1 mole) of tert-butyl 2-methoxyimino-3-oxobutyrate, and 27.0 g (0.2 mole) of sulfuryl chloride was added dropwise at 0° to 5° C. over a period of 1 hour and 30 minutes and stirred at 25° to 30° C. for 25 hours. After completion of the reaction, 25 ml of water was added and then stirred to conduct washing, whereby water-soluble by-products were removed.

Subsequently, the organic layer was dried over anhydrous magnesium sulfate, after which the solvent was distilled off under reduced pressure and 60 ml of n-hexane was added to the residue to extract and remove impurities. The residual n-hexane was distilled off under reduced pressure to obtain 10.1 g of 4-chloro-2-methoxyimino-3-oxobutyric acid as a yellow, oily substance (yield: 56.3%). On analysis, the purity of the desired compound was found to be 88.7%.

The present invention is markedly effective in that it makes it possible to produce a 4-halogeno-2-alkoxyimino-3-oxo fatty acid by use of a 2-alkoxyimino-3-oxo fatty acid ester as starting material easily in high yield by realizing simplification of the production procedure and prevention of the decomposition of unhalogenated fatty acid by carrying out, by one-pot one-step, ester decomposition reaction and halogenation reaction which have heretofore been carried out as two independent steps.

What is claimed is:

1. A one-pot one-step process for producing a 4-halogeno-2-alkoxyimino-3-oxo fatty acid of the formula:

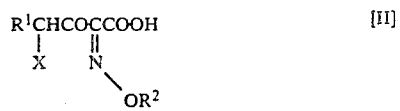

wherein X is a halogen atom; R$^1$ is a hydrogen atom, a linear or branched alkyl group selected from the group consisting of methyl, ethyl, propyl, isopropyl, tert-butyl, octyl and dodecyl, a cyclic alkyl group selected from the group consisting of cyclopropyl, cyclopentyl and cyclohexyl, an aryl group selected from the group consisting of phenyl, tolyl, xylyl and naphthyl or an aralkyl group selected from the group consisting of benzyl and phenethyl; and R$^2$ is a substituted of unsubstituted, linear or branched alkyl group selected from the group consisting of methyl, methoxymethyl, methylthiomethyl, ethyl, isopropyl, tert-butyl, octyl and dodecyl, a substituted or unsubstituted cyclic alkyl group selected from the group consisting of cyclopropyl, cyclopentyl and 4-methylcyclohexyl, a substituted or unsubstituted aryl group selected from the group consisting of phenyl, 4-chlorophenyl, 2-methoxyphenyl, tolyl, xylyl and napthyl, or a substituted or unsubstituted aralkyl group selected from the group consisting of benzyl, 4-chlorophenyl, 2-methoxybenzyl and phenethyl, consisting essentially of reacting a halogenating agent with a 2-alkoxyimino-3-oxo fatty acid ester of the formula:

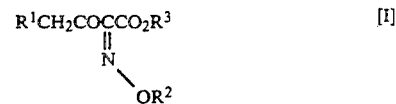

wherein R$^1$ and R$^2$ are as defined above, and R$^3$ is a tertiary alkyl group selected from the group consisting of tert-butyl, tert-amyl and 1,1-dimethylbutyl, in an ether solvent or a mixed solvent of an ether solvent and an inert organic solvent, and thereby carrying out cleavage of the ester linkage and halogenation of the carbon at the 4-position.

2. A process for producing a 4-halogeno-2-alkoxyimino- 3-oxo fatty acid according to claim 1, wherein in the formula [I] and the formula [II], R$^1$ is a hydrogen atom and R$^2$ is a methyl group.

3. A process for producing a 4-halogeno-2-alkoxyimino-3-oxo fatty acid according to claim 1, wherein $R^3$ in the formula [I] is a tert-butyl group.

4. A process for producing a 4-halogeno-2-alkoxyimino-3-oxo fatty acid according to claim 1, wherein the ether solvent is diisopropyl ether.

5. A process for producing a 4-halogeno-2-alkoxyimino-3-oxo fatty acid according to claim 1, wherein the inert organic solvent is a halogenated hydrocarbon.

6. A process for producing a 4-halogeno-2-alkoxyimino-3-oxo fatty acid according to claim 1, wherein the halogenating agent is chlorine or bromine.

7. A process for producing a 4-halogeno-2-alkoxyimino-3-oxo fatty acid according to claim 1, wherein in the formulae [I] and [II] $R^1$ is a hydrogen atom; $R^2$ is a methyl group; and $R^3$ is a tert-butyl group.

8. A process for producing a 4-halogeno-2-alkoxyimino-3-oxo fatty acid according to claim 1, wherein in the formulae [I] and [II] $R^1$ is a hydrogen atom; $R^2$ is a methyl group; and $R^3$ is a tert-butyl group, and the ether solvent is diisopropyl ether.

9. A process for producing a 4-halogeno-2-alkoxyimino-3-oxo fatty acid according to claim 1, wherein in the formulae [I] and [II] $R^1$ is a hydrogen atom; $R^2$ is a methyl group; and $R^3$ is a tert-butyl group, the ether solvent is diisopropyl ether and the halogenating agent is chlorine or bromine.

* * * * *